(12) United States Patent
Hiranaka et al.

(10) Patent No.: US 8,828,734 B2
(45) Date of Patent: Sep. 9, 2014

(54) NITRIC OXIDE DETECTION ELEMENT AND PROCESS FOR PRODUCING SAME

(75) Inventors: Kouichi Hiranaka, Ehime (JP); Toyofumi Nagamatsu, Ehime (JP); Yoshihiko Sadaoka, Ehime (JP); Yoshiteru Itagaki, Ehime (JP)

(73) Assignees: Panasonic Healthcare Co., Ltd., Ehime (JP); National University Corporation Ehime University, Ehime (JP)

( * ) Notice: Subject to any disclaimer, the term of this patent is extended or adjusted under 35 U.S.C. 154(b) by 11 days.

(21) Appl. No.: 13/814,155

(22) PCT Filed: Jul. 12, 2011

(86) PCT No.: PCT/JP2011/003986
§ 371 (c)(1),
(2), (4) Date: Feb. 4, 2013

(87) PCT Pub. No.: WO2012/017605
PCT Pub. Date: Feb. 9, 2012

(65) Prior Publication Data
US 2013/0137184 A1 May 30, 2013

(30) Foreign Application Priority Data

Aug. 3, 2010 (JP) ................. 2010-174335

(51) Int. Cl.
*G01N 21/77* (2006.01)
*G01N 1/22* (2006.01)
*G01N 33/00* (2006.01)
*G01N 31/22* (2006.01)
*G01N 21/78* (2006.01)

(52) U.S. Cl.
CPC .......... *G01N 21/783* (2013.01); *G01N 33/0037* (2013.01); *G01N 31/224* (2013.01)
USPC ............. 436/116; 436/84; 436/164; 436/165; 436/166; 436/167; 436/181; 422/82.09; 422/83; 422/88; 422/91; 73/23.2; 356/437

(58) Field of Classification Search
CPC ....... G01N 21/75; G01N 21/77; G01N 21/78; G01N 21/783; G01N 31/22; G01N 31/223; G01N 31/224; G01N 33/0037; G01N 33/497
USPC ........... 436/84, 106, 116, 164, 165, 166, 167, 436/181; 422/82.05, 82.09, 83, 88, 91, 84, 422/85; 73/23.2, 23.3; 356/432, 437
See application file for complete search history.

(56) References Cited

U.S. PATENT DOCUMENTS 5,603,820 A * 2/1997 Malinski et al. ............... 205/781
8,372,650 B2 * 2/2013 Toyoda .......................... 436/116

(Continued)

FOREIGN PATENT DOCUMENTS

EP  0 733 901 A2  9/1996
JP  49-008786  3/1974

(Continued)

OTHER PUBLICATIONS

International Search Report issued in International Patent Application No. PCT/JP2011/003986 dated Sep. 27, 2011.

(Continued)

*Primary Examiner* — Maureen Wallenhorst
(74) *Attorney, Agent, or Firm* — McDermott Will & Emery LLP

(57) ABSTRACT

Provided are a nitric oxide detection element capable of detecting NO gas contained in a mixed gas at a high speed even when the amount thereof is a super trace amount of ten and several parts per billion; and a process for producing the element. In a nitric oxide detection element having a substrate 12 and a sensing film 11 formed on a surface of the substrate, the sensing film is composed of nitric oxide sensing particles and a polymer adhesive. The nitric oxide sensing particles are produced by adsorbing a dye having a porphyrin skeleton and having, as a central metal, divalent cobalt onto surfaces of inorganic particles.

20 Claims, 11 Drawing Sheets

(56) References Cited

U.S. PATENT DOCUMENTS

| | | | |
|---|---|---|---|
| 8,623,281 B2 * | 1/2014 | Setayesh et al. | 422/82.01 |
| 2006/0003579 A1 | 1/2006 | Sir | |
| 2006/0177889 A1 | 8/2006 | Anvar et al. | |
| 2006/0177890 A1 | 8/2006 | Anvar et al. | |
| 2014/0037506 A1 * | 2/2014 | Miki et al. | 422/84 |

FOREIGN PATENT DOCUMENTS

| | | |
|---|---|---|
| JP | 2002-085969 A | 3/2002 |
| JP | 2002-222618 A | 8/2002 |
| JP | 2003-227800 A | 8/2003 |
| JP | 2006-090861 A | 4/2006 |
| JP | 2010-030944 A | 2/2010 |

OTHER PUBLICATIONS

Arai et al., "Optical Detection of Nitrogen Monoxide by Metal Porphine Dispersed in Amorphous Silica Film," Chemistry Letters, pp. 521-524, The Chemical Society of Japan, 1988.

Miyamoto et al., "Nitrogen Monoxide Adsorption and Contact Decomposition Properties of Co(II) Complexes," Journal of the Chemical Society of Japan, 1998, No. 5, pp. 338-345; w/partial English translation thereof.

* cited by examiner

NITRIC OXIDE DETECTION ELEMENT AND PROCESS FOR PRODUCING SAME

RELATED APPLICATIONS

This application is the U.S. National Phase under 35 U.S.C. §371 of International Application No. PCT/JP2011/003986, filed on Jul. 12, 2011, which in turn claims the benefit of Japanese Application No. 2010-174335, filed on Aug. 3, 2010, the disclosures of which Applications are incorporated by reference herein.

TECHNICAL FIELD

The present invention relates to a nitric oxide detection element used to detect a trace amount of nitric oxide contained in a mixed gas; and a process for producing the element.

BACKGROUND ART

Since the finding that nitric oxide (hereinafter, nitric oxide may also be referred to as NO) acts as an essential component of a muscle-relaxing factor, the physiological function of NO has been elucidated, and utilization of NO as a neurotransmitter or an infection marker has been under consideration.

In particular, analysis of NO gas in exhaled air has been attracting attention as a marker for airway inflammation caused by, for example, asthma or an allergy, the patients of which are increasing in recent years. This type of analysis allows noninvasive diagnosis of disease without imposing a burden on patients. The concentration of NO gas in exhaled air of normal adults is 2 ppb to 20 ppb, but is known to increase by a factor of approximately three in cases of airway inflammation caused by, for example, asthma or an allergy. The concentration of NO gas in exhaled air of children is lower than that of normal adults. Therefore, in cases of children, it is necessary to measure the concentration of a trace amount of NO gas in their exhaled air. If a simple and compact measurement device capable of measuring a trace concentration of NO gas is realized, the device can be used in determining the degree of airway inflammation of a patient or in determining treatment plans for asthma such as a dosage of asthma medication.

Conventionally, measurement of NO gas in exhaled air is performed in the following manner: cause a reaction between a patient's exhaled air and ozone under a reduced pressure, thereby causing excitation of part of NO gas contained in the exhaled air; and detect light that is emitted when the excited state returns to the ground state. However, such a chemiluminescence method requires expensive peripheral devices such as an ozone generator, and the maintenance of such devices is laborious.

An inexpensive and compact NO gas measurement device that is excellent in terms of gas selectivity, capable of quick measurement, and has high sensitivity is necessary for allowing asthma patients to measure the concentration of NO gas in their exhaled air everyday at a hospital or at home for self asthma management.

In recent years, there has been disclosed a method in which cobalt tetrakis(5-sulfothienyl)porphyrin (hereinafter, referred to as Co{T(5-ST)P}) contained in a silica film fabricated through a sol-gel process is reacted with NO gas in a vacuum chamber, and NO coordinated to Co{T(5-ST)P} is detected by using an ultraviolet and visible spectrophotometer (see, for example, Non Patent Literature 1).

In this method, in order to achieve necessary NO gas selectivity, an amorphous silica film containing Co {T(S-ST)P} is formed in the following manner: slowly hydrolyze ethyl silicate for 24 hours in the presence of Co {T(S-ST)P}; apply a resultant solution onto a glass substrate; and dry the glass substrate. The film formed in this manner is used as a NO sensor. This method has succeeded in detecting 17 ppm of NO gas with a sensor temperature of 200° C.

Further, there has been disclosed a method in which a porous glass plate is immersed in a chloroform solution containing cobalt tetraphenylporphyrin (5,10,15,20-tetraphenyl-21H,23H-porphyrin cobalt (hereinafter, referred to as CoTPP)), and is then dried. In this manner, a NO sensor in which the porous glass plate has CoTPP supported thereon is formed (see, for example, Non Patent Literature 2). According to the disclosure, the sensor is placed in a reactor that has been vacuum-evacuated by an oil diffusion pump, and NO gas is detected by means of an infrared spectrophotometer or an ultraviolet and visible spectrophotometer.

Still further, there has been disclosed a method of optically detecting NO gas by using a NO sensor which is a sol-gel glass having cytochrome C included therein (see, for example, Patent Literature 1).

In the meantime, a report is made not about NO gas but about a gas detecting tape wherein silica gel particles impregnated with a reagent exhibiting a color to a gas to be detected are fixed to an adhesive layer (see, for example, Patent Literature 2).

CITATION LIST

Patent Literatures

PTL 1: Japanese National Phase PCT Laid-Open Publication No. 2008-530527
PTL 2: JP-A-2003-227800

Non Patent Literatures

NPL 1: Hiromichi ARAI et al., "Optical Detection of Nitrogen Monoxide by Metal Porphine Dispersed Amorphous Silica Film", CHEMISTRY LETTERS of the Chemical Society of Japan, 1988, pp. 521-524
NPL 2: Makoto MIYAMOTO and Yoshio HANAZATO, "Nitrogen Monoxide Adsorption and Contact Decomposition Properties of Co(II) Complexes", Journal of the Chemical Society of Japan, 1998, No. 5, pp. 338-345

SUMMARY OF INVENTION

Technical Problem

According to a sensor using an amorphous silica film based on a conventional sol-gel process or a porous glass plate and porphyrin, a trace amount of NO gas can be detected with good sensitivity. However, porphyrin, which is a detecting agent, is contained in the amorphous silica film or carried in fine pores in the surface of the porous glass plate; thus, much time is required for adsorbing or desorbing NO gas onto/from the detecting agent. Thus, there is caused a problem that at the time of detecting a super trace amount of NO gas, the amount being at a level of ten and several parts per billion, the response time becomes long so that the gas cannot be detected at a high speed.

In light of the above-mentioned situation, an object of the present invention is to provide a nitric oxide detection element capable of detecting NO gas contained in a mixed gas at a high speed even when the amount thereof is a super trace amount of ten and several parts per billion; and a process for producing the element.

Solution to Problem

The present invention relates to a nitric oxide detection element, including a substrate, and a sensing film formed on a surface of the substrate, wherein the sensing film is made of nitric oxide sensing particles and a polymer adhesive, and the nitric oxide sensing particles are formed by adsorbing a dye having a porphyrin skeleton and having as a central metal divalent cobalt onto surfaces of inorganic particles.

With the nitric oxide detection element of the present invention, NO gas can be precisely detected at a high speed even when the concentration thereof is a super trace amount of several parts per billion to ten and several parts per billion. This would be for the following reason: In the present invention, cobalt porphyrin is adsorbed onto surfaces of the inorganic particles, and these particles are fixed onto the substrate surface with a polymer adhesive, whereby NO gas easily approaches cobalt porphyrin. Thus, not the diffusion of NO gas but a reaction thereof on the particle surfaces comes into a rate-determining stage to make it possible to quickly increase coordinate bonds between cobalt, which is the central metal of porphyrin, and NO gas, the bonds being accompanied by charge transfer. However, in any conventional structure, porphyrin is contained in an amorphous silica film or carried in fine pores in a surface of a porous glass plate; thus, it takes much time that NO gas approaches cobalt. It appears that the diffusion of NO gas is in a rate-determining stage.

The present invention also relates to a nitric oxide detector, including the aforementioned nitric oxide detection element, a gas introducing part for bringing a surface of the sensing film of the nitric oxide detection element into contact with a measurement gas possibly containing nitric oxide, a phototransmitter for radiating light to the sensing film, and a photoreceiver for receiving light reflected on the sensing film or light transmitted through the sensing film.

The present invention further relates to a nitric oxide detection method, including a first step of initializing the aforementioned nitric oxide detection element, a second step of radiating, after the first step, light to the sensing film of the nitric oxide detection element, and measuring the optical absorptance of the sensing film, a third step of bringing, after the second step, the sensing film into contact with a measurement gas possibly containing nitric oxide, a fourth step of radiating, after the third step, light to the sensing film and measuring the optical absorptance of the sensing film, and a fifth step of comparing the optical absorptance obtained in the fourth step with the optical absorptance obtained in the second step to determine the concentration of nitric oxide contained in the measurement gas.

The present invention further relates to a process for producing a nitric oxide detection element, including a step of applying, onto a surface of a substrate, a polymer adhesive solution wherein a polymer adhesive is dissolved in a first solvent, a step of mixing a dye having a porphyrin skeleton and having, as a central metal, divalent cobalt with inorganic particles and a second solvent to produce a preparation solution containing nitric oxide sensing particles wherein the dye is adsorbed onto surfaces of the inorganic particles, and the second solvent, a step of adding the preparation solution to the polymer adhesive solution applied onto the surface of the substrate, and a step of drying the first solvent and the second solvent to form, onto the substrate, a sensing film made of the nitric oxide sensing particles and the polymer adhesive.

Advantageous Effects of Invention

With the nitric oxide detection element of the present invention, NO gas can be precisely detected at a high speed even when the concentration thereof is a super trace amount of several parts per billion to ten and several parts per billion.

DESCRIPTION OF EMBODIMENTS

Hereinafter, a nitric oxide detection element and a production process thereof according to the present invention are described based on embodiments.

Figure 1:
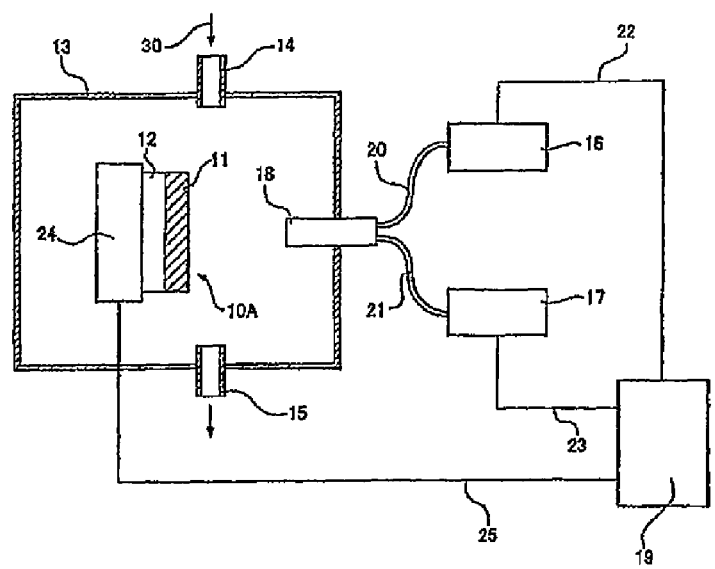
FIG. 1 is a conceptual diagram showing a configuration of a nitric oxide detector which includes a nitric oxide detection element of the present invention.

FIG. 1 is a conceptual diagram illustrating a configuration of a nitric oxide detector including a nitric oxide detection element 10A of the present invention.

The nitric oxide detection element 10A is composed of a substrate 12, such as a transparent plastic substrate, and a sensing film 11 fixed onto a surface of the substrate 12. The sensing film is composed of inorganic particles having, on surfaces thereof, an adsorbed dye and a polymer adhesive, and is preferably composed of the two and a non-ionic surfactant. The dye is, for example, cobalt tetramethoxyphenylporphyrin $CoTP(OCH_3)_4P$ (available from Tokyo Chemical Industry Co., Ltd.) having divalent cobalt as a central metal. The inorganic particles may be, for example, particles NIPGEL (trade name) available from Tosoh Silica Corporation. It is preferred to use, as the inorganic particles, particles subjected to water-repellent treatment. The polymer adhesive is, for example, hydroxypropylcellulose (referred to as HPC, and available from Sigma-Aldrich Co.). The non-ionic surfactant is, for example, Triton X-100 (trade name, available from GE Healthcare UK Ltd.).

This nitric oxide detection element 10A is disposed within a measurement cell 13. Measurement gas 30, which possibly contains nitric oxide (NO), is introduced into the measurement cell 13 through a gas introducing inlet 14 and is then discharged from a gas exhaust outlet 15. During this process, the surface of the sensing film 11 is exposed to the measurement gas 30.

The nitric oxide measurement device shown in FIG. 1 is of a light-reflection type. For the purpose of detecting a change in optical properties of the sensing film 11 before and after the sensing film 11 is exposed to the measurement gas 30, a photo transmitter/photoreceiver 18 is disposed such that the photo transmitter/photoreceiver 18 is opposed to the nitric oxide detection element 10A in the light-reflection type nitric oxide measurement device. The photo transmitter/photoreceiver 18 is connected to a light source 16 via an optical fiber 20, and is connected to a photodetector 17 via another optical fiber 21. Light from the light source 16 (preferably, light having an optical wavelength range including 400 nm to 450 nm) is emitted from the photo transmitter/photoreceiver 18 and perpendicularly falls on the sensing film 11 of the nitric oxide detection element 10A. The light is reflected by the surface of the sensing film 11 and is then incident on the photo transmitter/photoreceiver 18. Thereafter, the light is guided to the photodetector 17.

As one example, the photodetector 17 includes a CCD and a diffraction grating such as a prism or a grating. Alternatively, the photodetector 17 may include an optical band-pass filter, a silicon photodiode, a photocurrent-voltage conversion circuit, and an amplifier circuit (not shown). Regardless of which of the above configurations is applied to the photodetector 17, the detection light is converted into a light detection signal corresponding to the amount of reflected light, and then measured.

Since a temperature controller 24 is provided within the measurement cell 13, the internal temperature of the measurement cell 13 can be controlled. The temperature controller 24 includes a heater and a thermocouple for use in temperature detection (not shown). The light source 16, the photodetector 17, and the temperature controller 24 are connected to a measurement controller 19 via control lines 22, 23, and 25, respectively, so that the operations of the light source 16, the photodetector 17, and the temperature controller 24 can be controlled.

Although in the above description the phototransmitter and the photoreceiver are integrally formed together, the phototransmitter and the photoreceiver may be provided as separate components. In a case where the substrate is formed of a transparent material, the phototransmitter and the photoreceiver may be disposed such that they face each other with the nitric oxide detection element 10A positioned therebetween.

Figure 2:
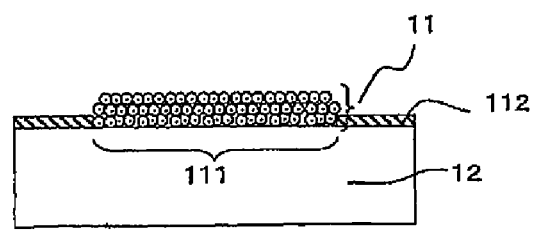
FIG. 2 is a cross-sectional conceptual diagram showing a nitric oxide detection element of the present invention.

FIG. 2 is a cross-sectional conceptual diagram showing the nitric oxide detection element 10A. As shown in FIG. 2, a sensing film 11 is fixed on the surface of a substrate 12. Patterning is performed in advance on the surface of the substrate 12, and the surface is divided into a sensing film portion 111 and a peripheral portion 112. The sensing film 11 is formed on the sensing film portion 111.

Figure 3:
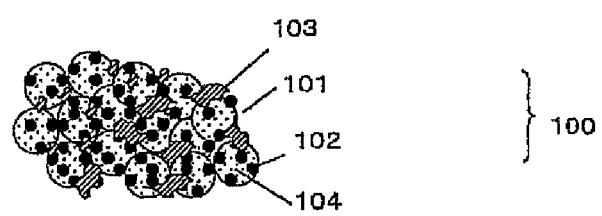
FIG. 3 is an enlarged conceptual diagram showing a relationship among materials forming a sensing film 11.

FIG. 3 is an enlarged conceptual diagram showing a relationship among materials forming the sensing film 11 of FIG. 2. As shown in FIG. 3, a dye 102 is supported on the surfaces of inorganic particles 101, and thus nitric oxide sensing particles 100 are formed. Preferably, a non-ionic surfactant 104 is used, the presence of which suppresses the dye 102 from aggregating together. Accordingly, the dye 102 is supported on the surfaces of the inorganic particles 101 in a dispersed manner. The nitric oxide sensing particles 100 are bound to each other via a polymer adhesive 103 to form a single body as the sensing film 11. The sensing film 11 is adhered to, and thereby fixed to, the surface of the substrate 12 also via the polymer adhesive 103.

The weight of the nitric oxide sensing particles 100 per unit area of the substrate 12 is preferably 0.2 mg/cm² to 2.0 mg/cm². If the weight per unit area is less than 0.2 mg/cm², then a change in the light spectrum with respect to a trace amount of NO gas decreases, resulting in insufficient NO sensitivity. If the weight per unit area exceeds 2.0 mg/cm², the adhesion of the sensing film 11 becomes weak, resulting in an increased possibility of occurrence of cracks in the sensing film 11.

Hereinafter, component materials forming the nitric oxide detection element are described in detail.

(Dye)

The present invention uses the dye 102 which contains a porphyrin complex. The porphyrin complex herein has a porphyrin skeleton which contains a metal at its center. The porphyrin skeleton may be modified by various substituents.

The light absorption spectrum of the porphyrin complex indicates Soret band (B-band) absorption in an optical wavelength region of 400 nm to 450 nm (ultraviolet light region) and Q-band absorption in an optical wavelength region of no less than 500 nm (visible light region). In selecting the porphyrin complex, a relationship between a molar absorption coefficient and a NO sensitivity may be taken into consideration. The oxidation-reduction potential of the central metal of the porphyrin complex affects binding between the central metal and NO gas. The Porphyrins, Volume III, edited by David Dolphin, Academic Press, Inc., pp. 14-15, teaches that generally speaking, the molar absorption coefficient in the Soret band is approximately $10^5$ ($M^{-1} \cdot cm^{-1}$) and the molar absorption coefficient in the Q-band is approximately $10^3$ ($M^{-1} \cdot cm^{-1}$).

The inventors of the present invention consider that in order to detect NO gas that is contained in exhaled air in a scale of several ppb to a few hundred of ppb, it is preferred to utilize changes in the absorption spectrum in the Soret band which has a large molar absorption coefficient, and studied this matter from various aspects. The molar absorption coefficient proportionally increases in accordance with an increase in NO sensitivity, that is, an increase in NO gas concentration. For this reason, it is preferred to use, among porphyrin complexes, a porphyrin complex having a symmetric molecular structure. The higher the degree of symmetry of the molecular structure of the porphyrin complex, the higher the absorption in the Soret band of the porphyrin complex, whereas the lower the degree of symmetry of the molecular structure of the porphyrin complex, the lower the absorption in the Soret band of the porphyrin complex. Although the absorption in the Q-band is less affected by the molecular structure of the porphyrin complex than the absorption in the Soret band, the molar absorption coefficient in the Q-band is equal to or less than $10^4$ ($M^{-1} \cdot cm^{-1}$), which is low.

Conceivable ways of increasing the NO sensitivity of the porphyrin complex include the following: (1) suitably select the central metal of the porphyrin complex and (2) change the substituents of the porphyrin skeleton, thereby donating electrons to a macrocyclic 7C conjugated system at the center of the porphyrin structure (i.e., electron-donating) and withdrawing electrons from the π conjugated system (i.e., electron-withdrawing).

(1) Central Metal

NO sensitivities of porphyrin complexes that contain iron (Fe), Mn (manganese), cobalt (Co), Ni (nickel), and Zn (zinc) as their respective central metals were examined. The results indicated that the porphyrin complexes containing respective central metal elements other than cobalt showed poor reactivity with NO gas, that is, they showed low NO sensitivity. In contrast, it was found that the porphyrin complex containing cobalt as a central metal showed high NO sensitivity. In the case of CO (II) TPP, the molar absorption coefficient of its Soret band is $2.8 \times 10^5$ ($M^{-1} \cdot cm^{-1}$) and the molar absorption coefficient in the Q-band is $1.2 \times 10^4$ ($M^{-1} \cdot cm^{-1}$). Accordingly, the present invention uses a porphyrin complex that contains divalent cobalt as a central metal. It is presumed that a difference in NO gas reactivity between the porphyrin complex containing divalent cobalt and the other porphyrin complexes containing various respective metals depends on a difference between the oxidation-reduction potential of a central metal and the oxidation-reduction potential of NO gas.

(2) Substituent

Next, a porphyrin complex of which the central metal is cobalt and of which the molecular structure has a high degree of symmetry was selected, and an influence of the substituents of the porphyrin skeleton on the NO sensitivity was examined. The structure of a cobalt porphyrin complex, CoTP(Xi)P, used in the examination is represented by a chemical formula shown below.

[Chemical Formula 1]

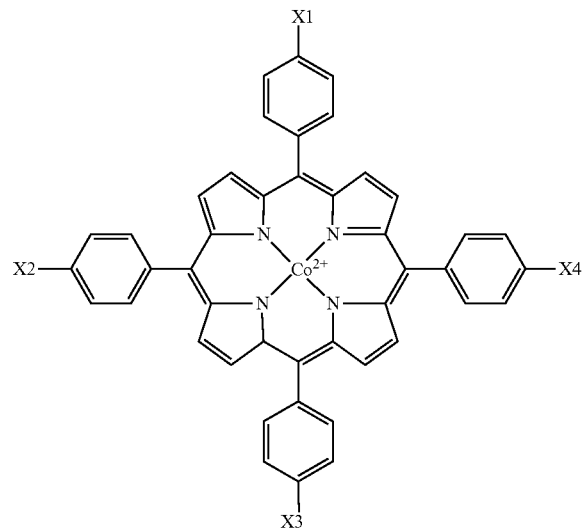

In the chemical formula, X1, X2, X3 and X4 each represent hydrogen (—H), a methoxy group (—OCH₃), or a hydroxyl group (—OH).

CoTP(Xi)P represented by the above formula is a porphyrin complex that contains divalent cobalt as a central metal and that has four phenyl groups on the outside of its porphyrin skeleton. Xi (i=an integer from 1 to 4) represents substituents bound to the phenyl groups, and the substituents are selected from hydrogen (—H), a methoxy group (—OCH₃), and a hydroxyl group (—OH).

In a case where Xi=—H, the cobalt porphyrin complex is cobalt tetraphenylporphyrin (5,10,15,20-tetraphenyl-21H,23H-porphyrin cobalt (CoTPP)). In a case where Xi=—OCH₃, the cobalt porphyrin complex is cobalt tetramethoxyphenylporphyrin (5,10,15,20-tetra(4-methoxyphenyl)-21H,23H-porphyrin cobalt (CoTP(4-OCH₃)P)). The same advantageous effects can be obtained by using a mixture of these compounds. The two compounds are soluble in a halogen-based solvent as a second solvent that will be described later. In a case where Xi=—OH, the cobalt porphyrin complex is cobalt tetrahydroxyphenylporphyrin (5,10,15,20-tetra(4-hydroxyphenyl)-21H,23H-porphyrin cobalt (CoTP(4-OH)P)). This porphyrin is soluble in an alcohol-based solvent as the second solvent, which will be described later.

From the examination, it has been found that if the substituents of the porphyrin complex are hydrogen, the methoxy group, or the hydroxyl group, then the NO sensitivity indicated by the porphyrin complex increases in the order of hydrogen, the methoxy group, and the hydroxyl group.

(Non-Ionic Surfactant)

The non-ionic surfactant 104 may be used for the purpose of suppressing the dye 102 from aggregating, and sufficiently dispersing the dye 102. For such purposes, the non-ionic surfactant is preferably one, the hydrophilic-lipophilic balance (HLB value: a numerical value indicating the degree of affinity of a surfactant for water and oil) of which is not lower than 13 and not higher than 15. As a nonlimiting example, use of Triton X-100 (trademark, available from GE Healthcare UK Ltd.), the HLB value of which is 13.5, is preferred.

As an alternative, a hydrophilic non-ionic surfactant and a lipophilic non-ionic surfactant may be mixed together at a suitable composition ratio to form a non-ionic surfactant mixture that indicates an HLB value suitable for use in the present invention. The non-ionic surfactant mixture thus prepared may be used. In this case, for example, TWEEN80 (available from Tokyo Chemical Industry Co., Ltd.) may be selected as a hydrophilic non-ionic surfactant, and SPAN80 (available from Tokyo Chemical Industry Co., Ltd.) may be selected as a lipophilic non-ionic surfactant. By mixing these surfactants together at a suitably adjusted composition ratio, the same surfactant performance as that of Triton X-100 can be achieved.

(Inorganic Particles)

Although the inorganic particles 101 are not limited to particular inorganic particles, inorganic particles such as silica particles or α-alumina particles are preferred. A mixture of silica particles and α-alumina particles may also be used.

Preferably, the inorganic particles used herein are water-repellent treated. A method used for treating the inorganic particles to have water repellency may be a publicly known conventional method. For example, water-repellent treated inorganic particles 101 can be obtained by causing a chemical reaction between a silane coupling agent and the aforementioned particles, or by boiling the particles with silicone oil. The degree of the water repellency of the water-repellent treated particles can be identified by means of an infrared spectrophotometer. In the case of silica particles, a sharp infrared ray absorption originating from silanol groups (—Si—OH) is observed near a wavenumber of 3540 cm$^{-1}$. The degree of the water-repellent treatment can be determined in accordance with that of the infrared ray absorption. In a case where such water-repellent treated inorganic particles are used in the present invention, when the inorganic particles are mixed with a solvent in a fabrication process of the nitric oxide detection element, the inorganic particles are well dispersed in the solvent and do not easily settle out. Accordingly, the dye 102 is sufficiently dispersed and thereby suppressed from aggregating, which makes it possible to improve the NO sensitivity of the nitric oxide detection element to be fabricated.

Preferably, the inorganic particles 101 have a particle diameter of 6 μm to 12 μm. The particle diameter can be measured by using a publicly known particle size distribution measurement apparatus, for example, LA-950 (available from HORIBA, Ltd.). In the measurement, an upper limit cumulative frequency median diameter $d_{90}$ and a lower limit cumulative frequency median diameter $d_{10}$ in a cumulative frequency distribution curve of particle size distribution obtained through a method compliant with JIS K 5600-9-3 (2006) are deemed to be an upper limit particle diameter and a lower limit particle diameter. Specifically, the particle diameter is not less than a cumulative frequency median diameter $d_{10}$ of 6 μm and not greater than a cumulative frequency median diameter $d_{90}$ of 12 μm in particle size measurement using a publicly known particle size distribution measurement apparatus (median diameters are such that $d_{10}$=6 μm and $d_{90}$=12 μm, and a mode diameter is 9 μm; hereinafter, the particle diameter is in the range of 6 μm to 12 μm, and an average particle diameter is the aforementioned mode diameter). In the present invention, silica particles, α-alumina particles, or a mixture of silica and α-alumina particles of which the particle diameter is in the aforementioned particle diameter range may be suitably used.

When particles having a diameter less than 6 μm are adhered to each other, they tend to detach from each other since the adhesion between the particles is weak. Moreover, in the case of using such particles having a diameter less than 6 μm, when the substrate 12 and the nitric oxide sensing particles 100 are adhered to each other, the adhesion tends to be weak. In this case, in order to obtain sufficient adhesion, it is desired that the polymer adhesive 103 is disposed between the particles, as well as between the substrate and the particles, and also, it is desired to increase the amount of usage of the polymer adhesive. However, an increase in the amount of usage of the polymer adhesive causes an extended NO response time, resulting in less prompt NO response. Therefore, it is preferred that the particle diameter is 6 μm or greater. If the particle diameter exceeds 12 μm, the NO sensitivity slightly increases. In this case, however, the NO response time is extended. The reason for this is that the greater the particle diameter, the more the particles tend to aggregate. Therefore, in order to satisfy both the NO sensitivity and the NO response time, it is preferred that the diameter of the water-repellent treated particles is not less than 6 μm and not greater than 12 μm.

(Polymer Adhesive)

The polymer adhesive 103 acts as an adhesive for adhering the nitric oxide sensing particles to each other to form the sensing film, and as an adhesive for adhering the nitric oxide sensing particles to the substrate 12.

Preferably, the glass transition temperature (hereinafter, referred to as Tg) of the polymer adhesive is in a range from −150° C. to 150° C. Polymer adhesives having the glass transition temperature within this range are excellent in gas permeability. The NO response time can be reduced when a polymer adhesive having excellent gas permeability is used. Adhesion of the sensing film 11 to the substrate 12 is insufficient when Tg is lower than −150° C. Gas permeability of the polymer adhesive becomes insufficient and the NO response time becomes extended when Tg exceeds 150° C.

Moreover, in fabricating the sensing film of the nitric oxide detection element, the polymer adhesive is preferably transparent against the detection light. In the case of using, as the detection light, light having an optical wavelength not shorter than 400 nm and not longer than 450 nm, the polymer adhesive is preferably transparent in an optical wavelength region of 400 nm to 450 nm.

Preferred examples of such a polymer adhesive include: hydroxypropylcellulose (referred to as HPC, Tg=19° C. to 125° C., and Tg depends on a molecular weight); polycarbonate-based urethane resin (available from Meisei Chemical Works, Ltd., Tg=−30° C. to 130° C.); polyethylene glycol (referred to as PEG, Tg=−115° C. to 86° C.); polyethylene oxide (referred to as PEO, Tg=−53° C.); acrylic resins such as polymethylisobutyl methacrylate (Tg=48° C.), poly(methyl acrylate) (Tg=66° C.), and polyacrylonitrile (Tg=97° C.); vinyl resins such as polystyrene (Tg=100° C.), polyvinyl chloride (Tg=81° C.), and polyvinyl alcohol (Tg=85° C.); polydimethylsiloxane (Tg=−123° C.); ethyl cellulose (Tg=43° C.); and biodegradable plastics such as polycaprolactone (Tg=−62° C.), polybutylene succinate (Tg=−33° C.), and polybutylene succinate adipate (Tg=−42° C.). It should be noted that examples of the polymer adhesive also include copolymers of those in the above examples that can be copolymerized. Examples of the polymer adhesive further include modified products of those in the above examples that can be modified by using a side-chain substitution product for the purpose of improving a refractive index, thermal resistance, or the like.

Any of the above polymer adhesives may be used in combination with a plasticizer, aiming at improving flowability. For example, dioctyl phthalate, which is a plasticizer, may be mixed into ethyl cellulose (Tg=43° C.), and the resultant mixture may be used as a substitute for PEO.

(Substrate)

Preferably, the substrate 12 is sheet-shaped and is formed of a thermal-resistant material that reflects the detection light or allows the detection light to pass through. If light having an optical wavelength not shorter than 400 nm and not longer than 450 nm is used as the detection light, it is preferred that the substrate 12 is formed of a material that reflects the light having an optical wavelength in the range of 400 nm to 450 nm or allows the light to pass through.

Examples of such a substrate include: plastic substrates such as thermal-resistant films, including a polyethylene terephthalate film (PET), a polyethylene naphthalate film (PEN, trademark, available from DuPont Teijin Films), and an ARTON film (ARTON, trademark, JSR Corporation); ceramic substrates such as a glass substrate, a quartz substrate, and an alumina substrate; metal substrates containing aluminum or silver as a main component; paper; woven fabrics; and nonwoven fabrics. A composite of these materials may also be used as the substrate. A metal film containing silver or aluminum as a main component may be formed on the surface of the substrate 12. Forming the sensing film 11 on the metal film makes it possible to reduce power consumption of a light source 16 of a phototransmitter.

Next, a description is given of an example of a fabrication method of the nitric oxide detection element 10A.

(1) Preparation of Polymer Adhesive Solution

A polymer adhesive solution is prepared by using "HPC" (available from Sigma-Aldrich Co.) as the polymer adhesive 103 and using an alcohol-based solvent (e.g., methyl alcohol, ethyl alcohol, isopropyl alcohol, or a mixed solvent of these) as a first solvent. The polymer adhesive used here is not limited to HPC, but may be any of the aforementioned compounds. Preferably, the concentration of the polymer adhesive solution is adjusted such that the weight ratio of the polymer adhesive to the inorganic particles described later is 0.07 g/g to 0.20 g/g. Specifically, HPC is dissolved in the first solvent such that the HPC concentration is 6 mg/mL. In addition, a droplet amount of the polymer adhesive solution and a droplet amount of a dye-containing preparation solution are adjusted. The dye-containing preparation solution is described below.

(2) Preparation of Dye-Containing Preparation Solution

As one example, the following are incorporated into a halogen-based solvent (such as chloroform or dichloromethane) as a second solvent to prepare a preparation solution: a dye $CoTP(4-OCH_3)P$ [cobalt tetramethoxyphenylporphyrin]; water-repellent treated silica particles having a particle diameter of 6 μm to 12 μm; and a non-ionic surfactant Triton X-100, having an HLB value of 13.5. The content of each of the components in the preparation solution is, for example, as follows: the molar concentration of $CoTP(4-OCH_3)_4P$ in the preparation solution is $3.3 \times 10^{-5}$ mol/L to $3.3 \times 10^{-4}$ mol/L; that of the water-repellent treated silica particles is 10 mg/mL to 100 mg/mL; and that of the non-ionic surfactant is 0.16 mg/mL to 30 mg/mL. The molar weight ratio of the dye to the water-repellent treated silica particles is $1.0 \times 10^{-6}$ mol/g to $1.0 \times 10^{-5}$ mol/g. The molar weight ratio of the dye to the non-ionic surfactant is $3.0 \times 10^{-6}$ mol/g to $3.0 \times 10^{-4}$ mol/g, preferably $3.3 \times 10^{-6}$ mol/g to $5.9 \times 10^{-5}$ mol/g. The weight ratio of the non-ionic surfactant to the inorganic particles is 0.05 g/g to 1 g/g.

(3) Patterning on Substrate

Preferably, the sensing film portion 111 is formed in advance by patterning on the surface of the substrate 12. By performing the patterning, a variation in the area of the sensing film can be reduced, which allows precise measurement of a trace amount of nitric oxide gas. Although photolithography or a printing process used in semiconductor processing may be used for the patterning, the patterning method is not limited thereto.

In the patterning, it is preferred that the peripheral portion 112 surrounding the sensing film portion is liquid-repellent treated, and the sensing film portion 111 is lyophilic-treated. Varying the substrate surface properties in this manner allows the sensing film 11 to be formed with high precision, which makes it possible to reduce a variation in the NO sensitivity of the sensing film 11.

Specific examples of a method of the patterning include methods (i) and (ii) as described below. In the method (i), the peripheral portion 112 is coated with a photoresist or a metal, such that only the sensing film portion 111 is exposed, and then plasma etching is performed on the sensing film portion by using a mixed gas containing oxygen gas as a main component, such that irregularity is formed on the surface of the sensing film portion 111. In the method (ii), a fluorine resin coating such as FS-1010 (trademark, Fluoro Technology), or a silicone oil coating, is formed on the peripheral portion 112. A particularly preferred method is that a PEN film substrate is used as the substrate 12 and an FS-1010 fluorine resin coating is formed on the peripheral portion 112. With any of the above methods, the sensing film portion 111 can be readily made lyophilic as compared to the peripheral portion 112. Such surface properties of the substrate 12 can be confirmed, for example, by a method in which pure water is dripped onto the surface and the pure water contact angle is measured by using a FACE contact angle meter of CA-C series available from Kyowa Interface Science Co., Ltd. As one example, the pure water contact angle on the fluorine resin coating of the peripheral portion 112 is 115° to 118° whereas the pure water contact angle on the sensing film portion 111 of the PEN substrate is 70° to 80°.

(4) Formation of Droplet Film from Polymer Adhesive Solution

First, the polymer adhesive solution prepared in the above (1) is dripped onto the sensing film portion 111 on which the patterning has previously been formed, and thereby a droplet film containing the polymer adhesive is formed. Specifically, 10 μL to 30 μL of the polymer adhesive solution (e.g., methyl alcohol in which HPC is dissolved) is dripped onto the sensing film portion 111 on which the patterning has been performed such that the diameter of the sensing film portion 111 is 8 mm.

When the dripping is performed, the first solvent of the polymer adhesive solution does not spread beyond the boundary between the liquid-repellent peripheral portion 112 and the lyophilic sensing film portion 111. Therefore, a polymer adhesive droplet film with little variation in its area can be realized. The droplet film formed by the dripping may be semi-dried or completely dried.

(5) Formation of Droplet Film as Sensing Film

Next, 10 μL to 30 μL of the dye-containing preparation solution prepared in the above (2) is dripped onto the polymer adhesive droplet film. At this time, the preparation solution does not spread beyond the boundary between the sensing film portion 111 and the peripheral portion 112, and convection between the first solvent and the preparation solution occurs at the surface of the sensing film portion 111. As a result, a uniform droplet-based sensing film containing the nitric oxide sensing particles is formed. The reason for this is that the specific gravity of the alcohol-based solvent which is the first solvent is lighter than the halogen-based solvent which is the second solvent. In a case where the diameter of the sensing film portion 111 is 8 mm, if the dripping amounts of both the first solvent and the second solvent are 30 μL or less, then the droplet-based sensing film is not formed beyond the aforementioned boundary, and thus the sensing film 11 with little variation in its area is realized.

(6) Drying and Fixing of Sensing Film

Next, the droplet-based sensing film on the substrate 12 is air-dried and solidified to form the sensing film 11. Temperature and humidity conditions for drying the droplet-based sensing film are not particularly limited. For example, the droplet-based sensing film may be dried by air drying (at a room temperature with a relative humidity of 50%), or may be dried at a temperature higher than the room temperature, or may be dried by being heated up on a hot plate, so long as alteration of the substrate, the polymer adhesive, or the dye is not caused.

Preferably, the dripping amounts of the polymer adhesive solution and the dye-containing preparation solution are adjusted such that the weight ratio of the polymer adhesive to the inorganic particles is 0.07 g/g to 0.20 g/g. If the ratio of the polymer adhesive is lowered, the adhesion force between the nitric oxide sensing particles becomes weak, which tends to cause the particles to detach from the nitric oxide detection element. Although the adhesion force between the particles increases in accordance with an increase in the polymer adhesive ratio, such an increase in the polymer adhesive ratio tends to result in an extended NO response time.

The following will describe a specific example of a NO detection method using the nitric oxide detection element 10A containing, as a dye, cobalt tetramethoxyphenylporphyrin, CoTP(4-OCH$_3$)P, which contains a methoxy group as a substituent; and results thereof.

Figure 4:
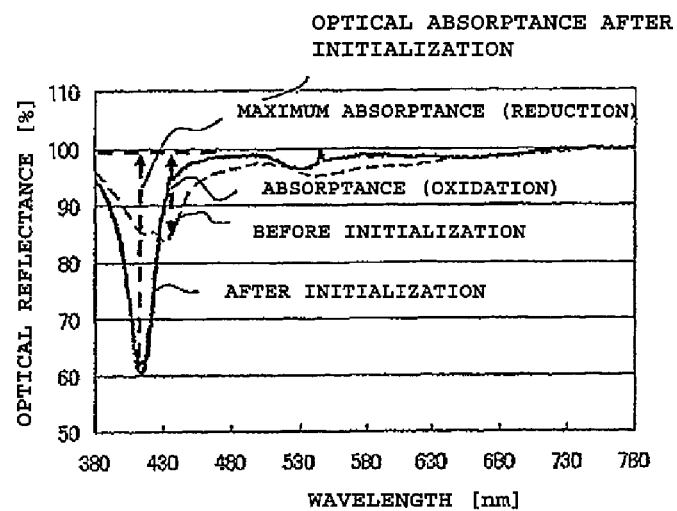
FIG. 4 is an ultraviolet and visible reflection spectrum shown by a nitric oxide detection element according to the present invention.

FIG. 4 is a graph showing an ultraviolet and visible reflection spectrum obtained which was obtained from a measurement using a spectrophotometer MCPD 7000 (available from Otsuka Electronics Co., Ltd.) and CoTP(4-OCH$_3$)P as a dye.

Prior to the measurement, heat treatment is performed for 10 minutes to initialize the nitric oxide detection element 10A. In the initialization, nitrogen gas (flow rate 100 mL/min) is flowed to the nitric oxide detection element 10A, with a sensor temperature set to 150° C. by the temperature controller 24. Through such initialization by heat treatment, a reflection spectrum derived from CoTP(4-OCH$_3$)P of which the central metal is divalent cobalt (hereinafter, referred to as Co(II)TP(4-OCH$_3$)P) is obtained, and the reflection spectrum has an absorption band having a central wavelength of 413 nm (the spectrum is indicated as "AFTER INITIALIZATION" in FIG. 4).

Next, the measurement cell 13 is stabilized for 10 minutes, during which nitrogen gas is flowed into the measurement cell 13 at a flow rate of 100 mL/min, with the sensor temperature set to 80° C. by the temperature controller 24. Thereafter, NO gas exposure is performed. When NO is bound to Co(II)TP (4-OCH$_3$)P, electrons in the d orbital of cobalt are coordinated while charge transfer to the unpaired electron orbital of NO is caused. As a result, cobalt is oxidized into trivalent cobalt. Consequently, the absorption band derived from Co(II)TP(4-OCH$_3$)P, which has a central wavelength of 413 nm, is attenuated as shown in FIG. 4. Also, an absorption band that is derived from CoTP(4-OCH$_3$)P containing trivalent cobalt (hereinafter, referred to as Co(III)TP(4-OCH$_3$)P) and that has a central wavelength of 438 nm (i.e., an absorption band in the spectrum indicated as "BEFORE INITIALIZATION" in FIG. 4) is increased. It should be noted that the present invention is not limited to the above specific sensor temperatures and treatment periods.

Figure 5:
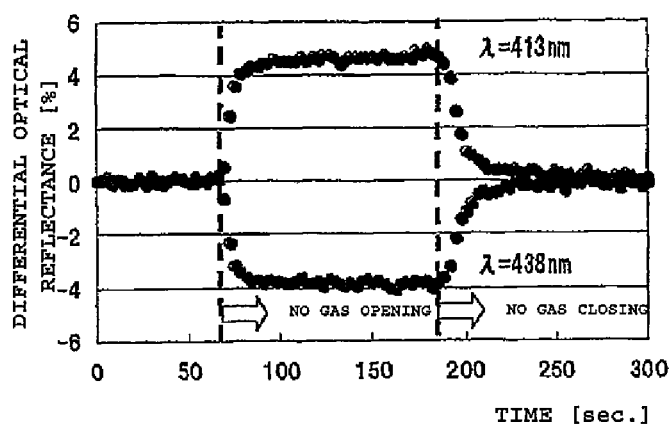
FIG. 5 is a graph showing changes in optical reflectance between before and after a nitric oxide detection element of the present invention is exposed to 1 ppm of NO gas.

FIG. 5 is a graph showing changes in optical reflectance between before and after an initialized nitric oxide detection element according to the present invention is exposed to NO gas. Specifically, the graph shows changes in optical reflectance at the wavelength of 413 nm derived from Co(II)TP(4-OCH$_3$)P and in optical reflectance at the wavelength of 438 nm derived from Co(III)TP(4-OCH$_3$)P). An optical reflectance defined as 100% in FIG. 5 is an optical reflectance at a wavelength of 470 nm in the light reflection spectrum of FIG. 4, at which wavelength the dye does not react with NO gas. FIG. 5 shows a value obtained by subtracting the optical reflectance at the optical wavelength of 413 nm after the NO gas exposure from the optical reflectance at the optical wavelength of 413 nm before the NO gas exposure, and a value obtained by subtracting the optical reflectance at the optical wavelength of 438 nm after the NO gas exposure from the optical reflectance at the optical wavelength of 438 nm before the NO gas exposure.

Conditions for the NO gas exposure at the time of the measurement are as follows: the sensor temperature is 80° C.; the concentration of nitrogen-diluted NO gas is 1 ppm of NO; and the flow rate of the NO gas is 200 ml/min. Hereinafter, a value obtained by subtracting the saturation value of the optical reflectance at the wavelength of 438 nm from the saturation value of the optical reflectance at the wavelength of 413 nm at the time of NO gas exposure, is referred to as a "differential optical reflectance". This differential optical reflectance depends on the NO concentration. Therefore, the NO concentration can be determined based on the differential optical reflectance of CoTP(4-OCH$_3$)P, which occurs from the NO exposure.

The present invention requires the sensing film 11 to contain CoTP(4-OCH$_3$)P containing divalent cobalt reactive with NO gas. The sensing film 11 may also contain CoTP(4-OCH$_3$)P containing trivalent cobalt in addition to CoTP(4-OCH$_3$)P containing divalent cobalt. A reflection spectrum obtained in a case where CoTP(4-OCH$_3$)P contains both divalent cobalt and trivalent cobalt is such that the absorption band derived from Co(II)(4-OCH$_3$)P and having a central wavelength of 413 nm and the absorption band derived from Co(III)(4-OCH$_3$)P and having a central wavelength of 438 nm, as shown in the reflection spectrum of FIG. 4, are combined.

When the nitric oxide detection element 10A fabricated by the above-described method reacts with oxygen (O$_2$) and carbon monoxide (CO) in the atmosphere, Co(III)(4-OCH$_3$)P becomes a major cobalt component. This hinders precise NO concentration measurement. Therefore, it is desired that the initialization through the heat treatment is performed on the nitric oxide detection element 10A prior to the measurement.

Specifically, in order to realize precise measurement of the concentration of a trace amount of NO gas, the sensing film 11 is initialized immediately before the NO gas measurement. In the initialization, cobalt in CoTP(4-OCH$_3$)P is transformed into divalent cobalt. The sensing film 11 may be initialized through the above-described heat treatment, or may be initialized through light irradiation onto the sensing film 11 or electromagnetic irradiation onto the sensing film 11 by microwaves. Moreover, these methods may be combined to perform the initialization.

When CoTP(4-OCH$_3$)P is heated up, gases such as O$_2$ and CO bound to CoTP(4-OCH$_3$)P are desorbed, and cobalt in CoTP(4-OCH$_3$)P is reduced to divalent cobalt. At the time of heating up CoTP(4-OCH$_3$)P, an inert gas such as N$_2$ gas or Ar gas, or air may be caused to flowed. By flowing such a gas, the desorbed gases such as O$_2$ and CO can be efficiently removed from the inside of the measurement cell 13.

The temperature and period of heating by means of the temperature controller 24 may be set appropriately so that the dye, the polymer adhesive, and the substrate will not be degraded and so that the heat treatment can be performed quickly. In particular, the sensor temperature at the time of performing the heat treatment is preferably in a range from 50° C. to 200° C. If the heating temperature in the initialization is less than 50° C., then the heat treatment period is extended in accordance with a decrease in the heating temperature. If the sensor temperature exceeds 200° C., it causes alteration of the polymer adhesive.

Figure 6A:
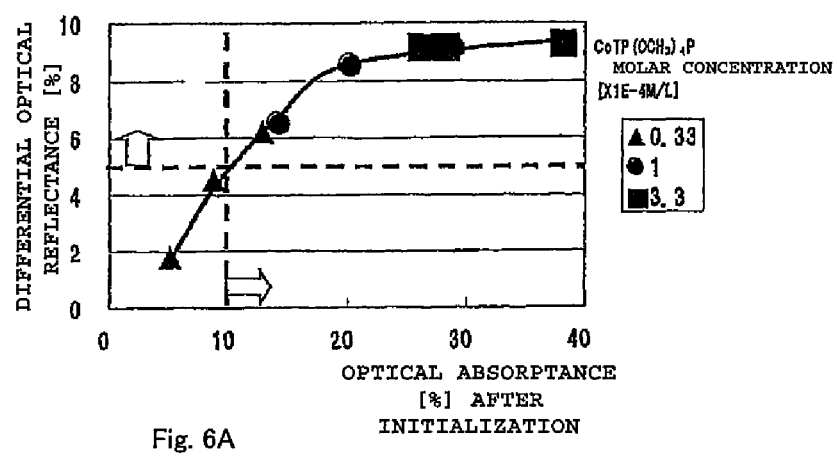
FIG. 6A and FIG. 6B are graphs showing a relationship between the optical absorptance and the NO sensitivity that are obtained from measurement made when the nitric oxide detection element of the present invention is exposed to 1 ppm of NO gas; and a relationship between the optical absorptance and the NO response time obtained therefrom.
Figure 6B:
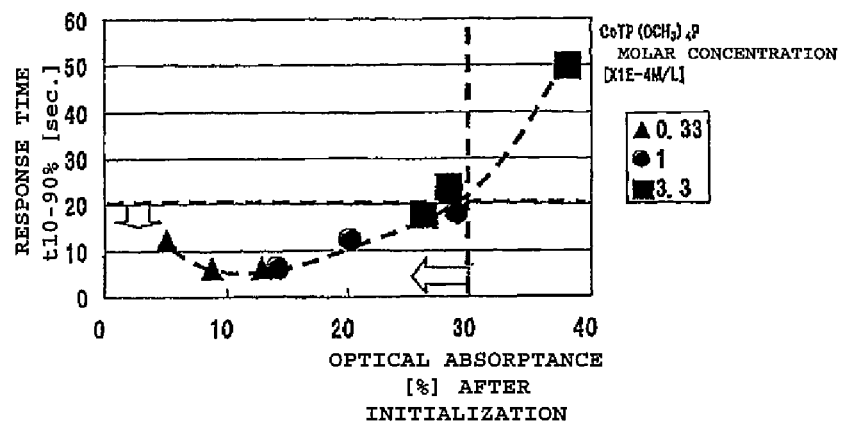

FIG. 6A and FIG. 6B are graphs showing a relationship between the optical absorptance after the heat treatment initialization and the NO sensitivity; and a relationship between the optical absorptance after the heat treatment initialization and the NO response time. The NO sensitivity is linear with respect to the differential optical reflectance. The differential optical reflectance that is represented by the vertical axis of FIG. 6A is a value obtained by subtracting "the saturation value of the reflectance at the wavelength of 438 nm" from "the saturation value of the reflectance at the wavelength of 413 nm" at the time of NO exposure shown in FIG. 5. An optical absorptance after initialization, represented by the horizontal axis, is obtained from the optical absorptance after the heat treatment initialization (=100%−minimum reflectance value). This optical absorptance reflects a loading amount of CoTP(4-OCH$_3$)P physically adsorbed onto the inorganic particles. That is, the less the optical absorptance, the less the loading amount, and the greater the optical absorptance, the greater the loading amount.

The vertical axis of FIG. 6B represents the NO response time, which is a period (seconds) required for 10% to 90% of the change in the differential optical reflectance at the wavelength of 413 nm shown in FIG. 5 to occur.

It is clear from FIG. 6A that, in a region where the optical absorptance after initialization is less than 20%, there is a linear relationship between the optical absorptance and the NO sensitivity. In other regions where the optical absorptance after initialization exceeds 20%, the NO sensitivity indicates a saturation trend.

According to asthma guidelines (American Thoracic Society Documents "ATS/ERS Recommendations for Standardized Procedures for the Online and Offline Measurement of Exhaled Lower Respiratory Nitric oxide and Nasal Nitric oxide, 2005"), it is required to detect and measure 2 ppb of NO gas in exhaled air within 10 seconds. In view of this, performance requirements for a nitric oxide detection element to be excellent in determining asthma are as follows: the differential optical reflectance, which corresponds to the NO sensitivity, is 5% or higher (first threshold); and the NO response time (10% to 90% value) is 20 seconds or shorter (second threshold). These requirements are applied as setting values in the description hereinafter. If the first threshold is satisfied, NO sensitivity requirements specified in the asthma guidelines can be met through a publicly known method as follows, that is: use an optical band-pass filter; increase the number of times of measurement sampling by an electrical circuit of the photodetector; and improve the signal/noise ratio of a detection circuit. In relation to the second threshold, the asthma guidelines specify a condition that the flow rate of exhaled air is 3000 mL/min. In the measurement conditions according to the present embodiment, the flow rate is 200 mL/min. Accordingly, with the flow rate specified by the asthma guidelines, collision probability between NO gas and divalent cobalt is increased by 15 times. If the NO response time of 20 seconds in the present embodiment is converted according to the condition specified by the guidelines, the NO response time becomes approximately 1.3 seconds. The above setting values are merely performance requirements for a nitric oxide detection element to be excellent in determining asthma. Even if a nitric oxide detection element fails to satisfy these setting values, it does not mean that the nitric oxide detection element is unusable.

It is clear from FIG. 6A that the optical absorptance that satisfies the first threshold, i.e., the optical absorptance that allows the differential optical reflectance corresponding to the NO sensitivity to be 5% or higher, is 10% or higher. It is clear from FIG. 6B that the optical absorptance that satisfies the second threshold, i.e., the optical absorptance that allows the NO response time to be 20 seconds or shorter, is 30% or lower. If the optical absorptance exceeds 30%, the NO response time becomes long. This is considered to be caused by dye aggregation. In view of these, in the present invention, the amount of CoTP(4-OCH$_3$)P loading on the inorganic particles is preferably such that the optical absorptance after initialization at an optical wavelength of 400 nm to 450 nm (Soret band) (maximum optical absorptance) is 10% to 30%.

Figure 7A:
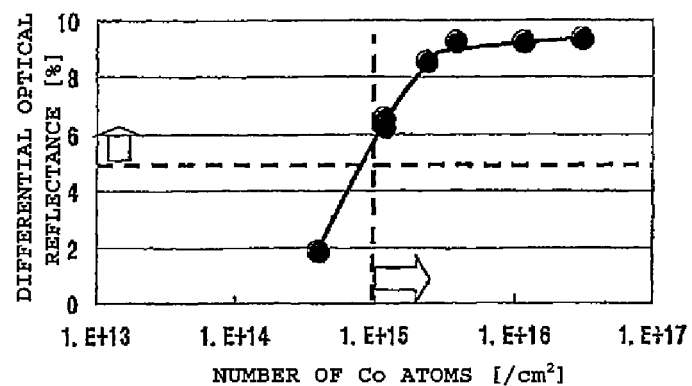
FIG. 7A and FIG. 7B are graphs showing a relationship between the number of cobalt atoms per unit area and the NO sensitivity that are obtained from measurement made when a nitric oxide detection element of the present invention is exposed to 1 ppm of NO gas; and a relationship between the number and the NO response time obtained therefrom.
Figure 7B:
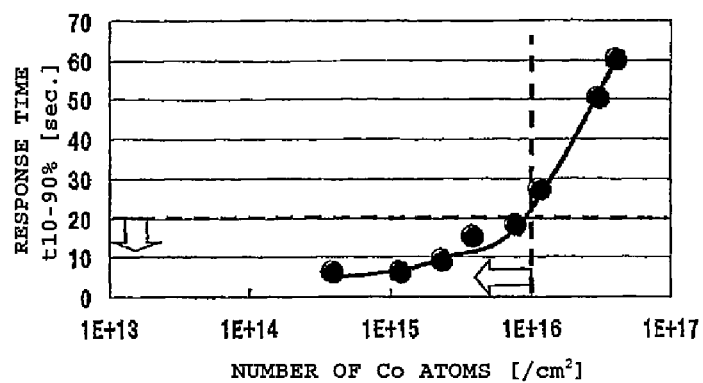

FIG. 7A and FIG. 7B show a relationship between the NO sensitivity and the number of cobalt atoms per unit area of the substrate surface of the nitric oxide detection element according to the present invention; and a relationship between the NO response time and the number of cobalt atoms per unit area of the substrate surface of the nitric oxide detection element according to the present invention. The number of cobalt atoms on the substrate surface can be measured by using a publicly known secondary ion mass spectrometer (abbreviated as SIMS). In FIG. 7A and FIG. 7B, the horizontal axis represents the number of cobalt atoms per unit area of the substrate surface, the surface area of which is defined by the above-described patterning and the property of which is varied by changing the CoTP(4-OCH$_3$)P concentration in the preparation solution. It is clear from FIG. 7A that the number of cobalt atoms is required to be $1 \times 10^{15}$/cm$^2$ or more in order to satisfy the first threshold of the NO sensitivity. It is clear from FIG. 7B that the number of cobalt atoms is required to be $1 \times 10^{16}$/cm$^2$ or less in order to satisfy the second threshold of the NO response time. In view of these, the number of cobalt atoms per unit area of the substrate surface is preferably $1 \times 10^{15}$/cm$^2$ to $1 \times 10^{16}$/cm$^2$. The NO sensitivity tends to decrease in accordance with a decrease in the number of cobalt atoms and become insufficient. The NO response time tends to be extended in accordance with an increase in the number of cobalt atoms. This is considered to be caused by dye aggregation.

Figure 8A:
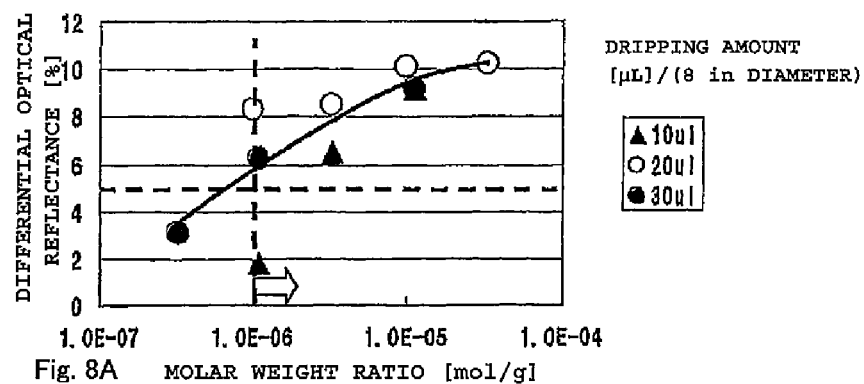
FIG. 8A and FIG. 8B are graphs showing a relationship between the molar weight ratio of a dye to inorganic particles and the NO sensitivity that are obtained from measurement made when a nitric oxide detection element of the present invention is exposed to 1 ppm of NO gas; and a relationship between the ratio and the NO response time obtained therefrom.
Figure 8B:
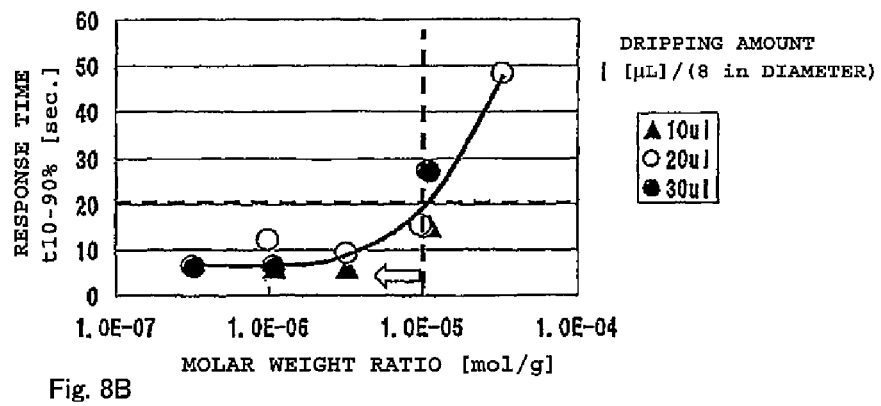

FIG. 8A and FIG. 8B show a relationship between the molar weight ratio of CoTP(4-OCH$_3$)P to water-repellent treated silica particles in a nitric oxide detection element of the present invention, and the NO sensitivity; and a relationship between the ratio and the NO response time. The data therein were obtained while the dripping amount of a preparation solution onto a PEN substrate having each sensing film portion having a diameter of 8 mm was varied into 10 µL, 20 µL or 30 µL. In FIG. 8A, its vertical axis represents the differential optical reflectance, and the horizontal axis represents the molar weight ratio (mol/g) of CoTP(4-OCH$_3$)P to the water-repellent treated silica particles. In FIG. 8B, its vertical axis represents the NO response time, and its horizontal axis is the same as in FIG. 8A. It is understood from FIG. 8A that the molar weight ratio of CoTP(4-OCH$_3$)P to the water-repellent treated silica particles, as the proportion of the loaded dye, needs to be $1.0 \times 10^{-6}$ mol/g or more in order that the first threshold of the NO sensitivity can be satisfied. It is also understood that when the dripping amount is 10 µL and the molar weight ratio is low, the dye is poor in dispersibility so that the NO sensitivity is deteriorated. It is understood from FIG. 8B that the molar weight ratio needs to be $1.0 \times 10^{-5}$ mol/g or less in order that the second threshold of the NO response time can be satisfied. When the molar weight ratio becomes larger, the NO response time tends to become longer. This would be because as the loading amount of the dye is larger, the dye further aggregates so that more time is required for response to NO.

Figure 9A:
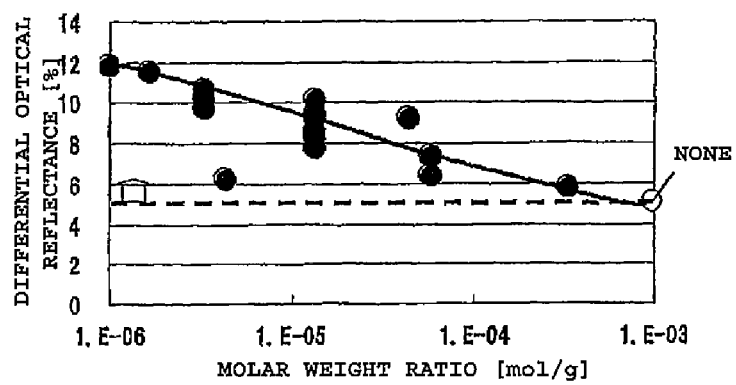
FIG. 9A and FIG. 9B are graphs showing a relationship between the molar weight ratio of a dye to a non-ionic surfactant and the NO sensitivity that are obtained from measurement made when a nitric oxide detection element of the present invention is exposed to 1 ppm of NO gas; and a relationship between the ratio and the NO response time obtained therefrom.
Figure 9B:
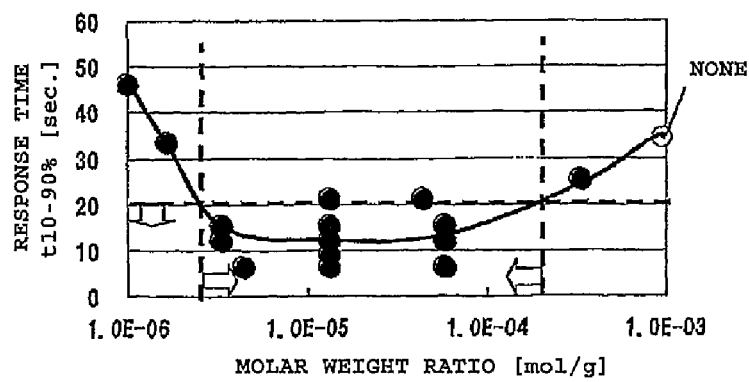

FIGS. 9A and 9B show a relationship between the molar weight ratio of CoTP(4-OCH$_3$)P to a non-ionic surfactant in a nitric oxide detection element of the present invention, and the NO sensitivity; and a relationship between the ratio and the NO response time. As the non-ionic surfactant, Triton X100, which has an HLB value of 13.5, is used. The same drawings also show data about a nitric oxide detection element produced without using water-repellent treated silica particles. It is understood from FIG. 9A that as the molar weight ratio is increased, the differential optical reflectance, which is the NO sensitivity, decreases. This is because the used amount of the non-ionic surfactant relative to that of the dye decreases so that the dye deteriorates in dispersibility to aggregate easily. It is understood from FIG. 9B that the molar weight ratio needs to be $3.0 \times 10^{-6}$ mol/g to $3.0 \times 10^{-4}$ mol/g, preferably $3.3 \times 10^{-6}$ mol/g to $5.9 \times 10^{-5}$ mol/g in order that the second threshold of the NO response time can be satisfied. Such use of a non-ionic surfactant in an appropriate amount makes it possible to improve the dye in dispersibility. Thus, a nitric oxide detection element can be obtained which shows a shorter NO response time. However, it is unessential to use a non-ionic surfactant. Even when this is not used, a nitric oxide detection element can be obtained which shows a relatively good NO sensitivity and a relatively good NO response time.

Figure 10A:
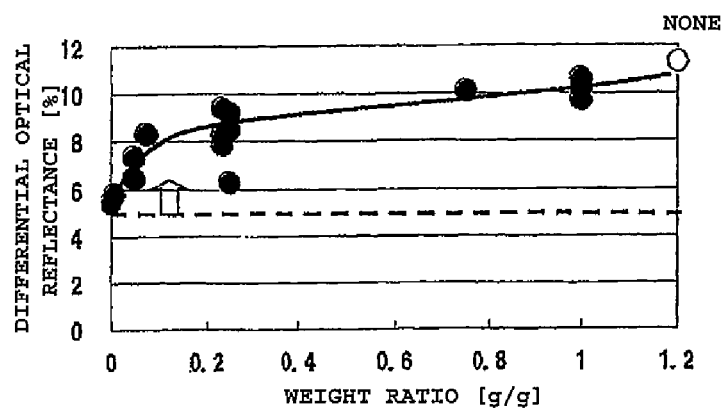
FIG. 10A and FIG. 10B are graphs showing a relationship between the weight ratio of a non-ionic surfactant to inorganic particles and the NO sensitivity that are obtained from measurement made when a nitric oxide detection element of the present invention is exposed to 1 ppm of NO gas; and a relationship between the ratio and the NO response time obtained therefrom.
Figure 10B:
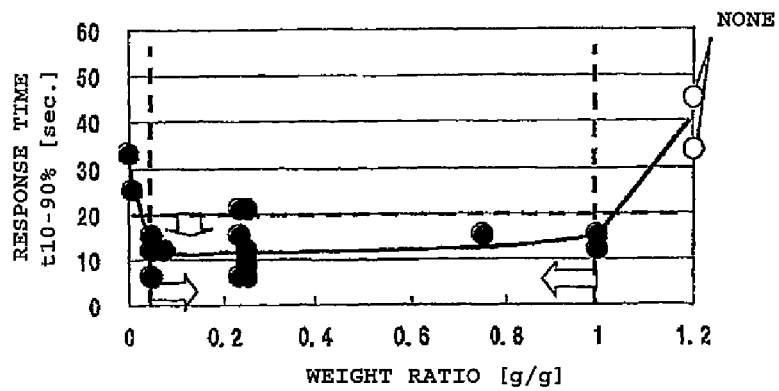
Figure 11:
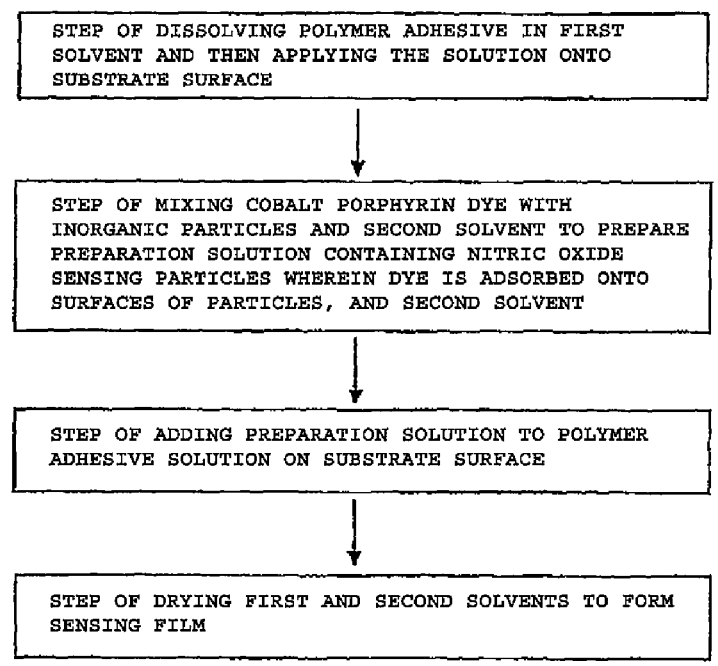
FIG. 11 is a flow chart showing a process for producing a nitric oxide detection element of the present invention.

FIGS. 10A and 10B show a relationship between the weight ratio of a non-ionic surfactant to water-repellent treated silica particles in a nitric oxide detection element of the present invention and the NO sensitivity; and a relationship between the weight ratio and the NO response time. The same drawings also show data about a nitric oxide detection element produced without using water-repellent treated silica particles. About conditions for producing a preparation solution, the molar concentration of CoTP(4-OCH$_3$)P is $1\times10^{-6}$ mol/L to $3.3\times10^{-4}$ mol/L, and the concentration of the water-repellent treated silica particles is 10 to 100 g/L. The dripping amount onto each sensing film portion having a diameter of 8 mm is 10 µL to 30 µL. It is understood from FIG. 10A that until the weight ratio reaches to 0.2 g/g, the differential optical reflectance, which is the NO sensitivity, increases abruptly, and thereafter the reflectance increases gently. According to FIG. 10B, the addition of the non-ionic surfactant causes a reduction in the NO response time (that is, a response to NO gas is attained at a higher speed), and when the weight ratio turns to 0.05 g/g or more, the response time comes to satisfy 20 seconds, which is the second threshold, or less. It is also understood that when the non-ionic surfactant is further increased so that the weight ratio exceeds 1 g/g, the NO response time exceeds 20 seconds. From the above, it is understood that the non-ionic surfactant not only improves CoTP(4-OCH$_3$)P in dispersibility as shown in FIG. 9 but also improves the water-repellent treated particles in dispersibility as shown in FIG. 10.

Next, in Table 1 are shown the following obtained by varying, in a nitric oxide detection element of the present invention, the weight ratio of a polymer adhesive to water-repellent treated silica particles and/or the average particle diameter of the particles: (1) the differential optical reflectance, which is the NO sensitivity, (2) the NO response time, and (3) a result obtained by evaluating the surface state of a produced sensing film.

About the surface state in the sensing film in the item (3), the state of exfoliation of the sensing film was observed with the naked eye after it was formed, and then evaluated in accordance with the following evaluation criterion.

4: Exfoliation was not observed at all in the sensing film.

3: Exfoliation was observed only at a peripheral portion of the sensing film.

2: Exfoliation was observed in the whole of the sensing film.

1: No sensing film was able to be formed so that observation of exfoliation was unable to be made.

On the basis of results of the items (1) to (3), each of the examples was synthetically judged in accordance with the following evaluation criterion.

4: The example was very good as a nitric oxide detection element.

3: The example was good as a nitric oxide detection element.

2: The example was permissible as a nitric oxide detection element.

1: The example was unable to be used as a nitric oxide detection element.

Hereinafter, a description will be made about production conditions and the evaluation results of each of the examples.

Example 1

As the water-repellent treated silica particles, particles having an average particle diameter of 1 µm (median diameter: $d_{10}$=0.7 µm, $d_{90}$=2 µm) were used. The molar concentration of CoTP(4-OCH$_3$)P in the preparation solution (second solvent: chloroform) was set to $1\times10^{-4}$ mol/L; and the ratio of the polymer adhesive (HPC) to the water-repellent treated particles to 6 g/90 g. The NO sensitivity satisfied the first threshold, but the NO response time was a relatively long period of 30 seconds not to satisfy the second threshold. However, this does not mean that the example is unusable as a nitric oxide detection element. When the surface state of the sensing film 11 was observed, the whole of the sensing film was cracked before exposed to NO. Thus, the state was estimated to be "2". From the above, the synthetic judgment thereof was estimated to be "2" as a nitric oxide detection element.

TABLE 1

| Sample | Average particle diameter (µm) | Polymer/ Particles (g/g) | Differential optical reflectance (%) | Response time (seconds) | Sensing film surface state | Synthetic judgment |
| --- | --- | --- | --- | --- | --- | --- |
| Example 1 | 1 | 6/90 = 0.067 | 7.7 | 30 | 2 | 2 |
| Example 2 | 1 | 6/60 = 0.10 | 7.1 | 9 | 3 | 3 |
| Example 3 | 1 | 6/30 = 0.20 | 6.5 | 9 | 3 | 3 |
| Example 4 | 9 | 6/90 = 0.067 | 8.9 | 18 | 3 | 3 |
| Example 5 | 9 | 6/60 = 0.10 | 8 | 9 | 4 | 4 |
| Example 6 | 9 | 6/30 = 0.20 | 6.7 | 6 | 4 | 4 |
| Example 7 | 9 | 12/30 = 0.40 | 10.8 | 40 | 4 | 2 |
| Example 8 | 14 | 6/90 = 0.067 | 8.3 | 18 | 2 | 2 |
| Example 9 | 14 | 6/60 = 0.10 | 7.7 | 12 | 3 | 3 |
| Example 10 | 14 | 6/30 = 0.20 | 7.2 | 9 | 4 | 4 |
| Comparative Example 1 | 9 | 0/30 = 0 | — | — | 1 | 1 |
| Comparative Example 2 | No silica | 10/0 | 11.5 | 50 | 4 | 1 |

In each of these examples, the concentration of the non-ionic surfactant in the preparation solution was fixed to 7.5 g per liter of chloroform, which is a second solvent. The differential optical reflectance was measured under conditions that the sensor temperature was 80° C., the nitrogen-diluted NO gas concentration was 1 ppm, and the flow rate was 200 mL/min.

Example 2

The same conditions as in Example 1 were used except that the ratio of the polymer adhesive (HPC) to the water-repellent treated particles was changed to 6 g/60 g. The NO sensitivity and the NO response time each satisfied the threshold. Since a peripheral portion of the sensing film was cracked into a middle degree, the surface state was estimated to be "3". The synthetic judgment thereof was estimated to be "3".

Example 3

The same conditions as in Example 1 were used except that the ratio of the polymer adhesive (HPC) to the water-repellent treated particles was changed to 6 g/30 g. The NO sensitivity and the NO response time each satisfied the threshold. Since a peripheral portion of the sensing film was cracked into a small degree, the surface state was estimated to be "3". The synthetic judgment thereof was estimated to be "3".

Example 4

The same conditions as in Example 1 were used except that particles having an average particle diameter of 9 μm (median diameter: $d_{10}=6$ μm, $d_{90}=12$ μm) were used as the water-repellent treated silica particles. The NO sensitivity and the NO response time each satisfied the threshold. Since a peripheral portion of the sensing film was cracked into a small degree, the surface state was estimated to be "3". The synthetic judgment thereof was estimated to be "3".

Example 5

The same conditions as in Example 4 were used except that the ratio of the polymer adhesive (HPC) to the water-repellent treated particles was changed to 6 g/60 g. The NO sensitivity and the NO response time each satisfied the threshold. No exfoliation was observed in the sensing film. Thus, the surface state thereof was good and estimated to be "4". The synthetic judgment thereof was estimated to be "4".

Example 6

The same conditions as in Example 4 were used except that the ratio of the polymer adhesive (HPC) to the water-repellent treated particles was changed to 6 g/30 g. The NO sensitivity and the NO response time each satisfied the threshold. No exfoliation was observed in the sensing film. Thus, the surface state was good and estimated to be "4". The synthetic judgment thereof was estimated to be "4".

Example 7

The same conditions as in Example 4 were used except that the ratio of the polymer adhesive (HPC) to the water-repellent treated particles was changed to 12 g/30 g. The NO sensitivity was larger than that in Example 6, but the NO response time was a relatively long period of 40 seconds not to satisfy the second threshold. The surface state of the sensing film was good. The synthetic judgment thereof was estimated to be "2". This is presumed as follows: the used amount of the polymer adhesive was increased relative to that of the water-repellent treated silica particles, so that the proportion of the nitric oxide sensing particles on which the polymer adhesive was adsorbed was increased; thus, the diffusion of NO gas came into a rate-determining stage so that the NO response time became long.

Example 8

The same conditions as in Example 1 were used except that particles having an average particle diameter of 14 μm (median diameter: $d_{10}=9$ μm, $d_{90}=22$ μm) were used as the water-repellent treated silica particles. The NO sensitivity and the NO response time each satisfied the threshold. The whole of the sensing film was cracked. Thus, the surface state was estimated to be "2". The synthetic judgment thereof was estimated to be "2".

Example 9

The same conditions as in Example 8 were used except that the ratio of the polymer adhesive (HPC) to the water-repellent treated particles was changed to 6 g/60 g. The NO sensitivity and the NO response time each satisfied the threshold. Since a peripheral portion of the sensing film was cracked into a small degree, the surface state was estimated to be "3". The synthetic judgment thereof was estimated to be "3".

Example 10

The same conditions as in Example 8 were used except that the ratio of the polymer adhesive (HPC) to the water-repellent treated particles was changed to 6 g/30 g. The NO sensitivity and the NO response time each satisfied the threshold. No exfoliation was observed in the sensing film. Thus, the surface state was good and estimated to be "4". The synthetic judgment thereof was estimated to be "4".

Comparative Example 1

The same silica particles as in Example 4 were used, and the molar concentration of $CoTP(4-OCH_3)P$ in the preparation solution (second solvent: chloroform) was set to $1\times10^{-4}$ mol/L, but no polymer adhesive was used. No sensing film was able to be formed. Accordingly, the synthetic judgment thereof was estimated to be "1".

Comparative Example 2

Without using silica particles, $CoTP(4-OCH_3)P$ was dispersed into a polymer adhesive HPC to form a sensing film. The NO sensitivity satisfied the threshold, but the NO response time became 50 seconds, which was a very long period. This is considered to be caused as follows: NO gas diffused into the polymer adhesive to reach the dye; thus, the diffusion came into a rate-determining step. It is understood that even when only a polymer adhesive is used without using silica particles in this way to produce a sensing film containing a dye, a nitric oxide detection element high in NO response speed cannot be produced. The synthetic judgment thereof was estimated to be "1".

It is understood from the aforementioned results in Table 1 that a nitric oxide detection element excellent in NO sensitivity and NO gas response time can be obtained by using cobalt porphyrin, a polymer adhesive and inorganic silica particles. It is understood that when the weight ratio of the polymer adhesive to the inorganic particles is, particularly, 0.07 to 0.20 g, a sensing film can be obtained which is good in surface state as well as in NO sensitivity and NO gas response time.

The above has described a case where the substituent of porphyrin is a methoxy group. However, the present invention is not limited to this case. The substituent may be a H group or an OH group. Hereinafter, a description will be made thereabout.

Experiment Example 1

A nitric oxide detection element was produced under the same conditions except that the cobalt porphyrin complex was changed to CoTPP wherein the substituent was H. The NO sensitivity turned smaller by about 25% as compared with that in a case where the optical absorptance was equal to that in the present example after the initialization of CoTP(4-OCH$_3$)P. However, the NO response time was substantially equivalent. The reason why this case was smaller in NO sensitivity than the case where the substituent was a methoxy group was that a H atom is smaller in electron donating performance to the large cyclic π conjugated system of the porphyrin skeleton than a methoxy group.

Experiment Example 2

A nitric oxide detection element was produced under the same conditions except that the cobalt porphyrin complex was changed to CoTP(OH)P wherein the substituent Xi was OH. In this case, an alcohol-based solvent (such as methyl alcohol or ethyl alcohol) was used as the second solvent of the preparation solution. The other production conditions were the same. This case was equivalent in both of NO sensitivity and NO response time to the case of CoTP(4-OCH$_3$)P.

As the polymer adhesive, a polycarbonate modified urethane resin, besides HPC, may be used. The sensor temperature is not limited to 80° C. However, the temperature is preferably not lower than 40° C. and not higher than 80° C., which is higher than an exhaled air temperature of 37° C.

Experiment Example 3

A polymer adhesive solution was prepared, using a polycarbonate modified urethane resin as the polymer adhesive, and using ethyl alcohol as the first solvent in a concentration of 6 mg/mL, and 10 μL thereof was dripped onto sensing film portions each having a diameter of 8 mm and formed beforehand into a pattern form on a PEN substrate. After the workpiece was air-dried (at a temperature of 23° C. and a relative humidity of 50%) for 30 seconds, a preparation solution described below was dripped onto the polymer adhesive droplet film, which was semi-dried.

As the cobalt porphyrin complex, CoTP(4-OCH$_3$)P and CoTPP were used in equimolar amounts. This mixture and 7.5 mg of a non-ionic surfactant, Triton X100, were dissolved in 1 mL of a chloroform solvent to prepare a preparation solution. About the molar concentration of the cobalt porphyrin complex, the total concentration of the two porphyrins was 1×10$^{-4}$ mol/L.

The preparation solution was dripped in an amount of 30 μL onto the semi-dried polymer adhesive layer. As a result, in the first solvent for dissolving the semi-dried polymer adhesive, and the second solvent of the preparation solution, even convection and drying started. At a temperature of 23° C. and a relative humidity of 50%, the workpiece was dried for 3 minutes to fix a sensing film 11. The produced nitric oxide detection element was set to the nitric oxide detector in FIG. 1, and a NO gas concentration test was made.

The temperature controller 24 was used to adjust the sensor temperature of the sensing film 11 to 150° C. While compressed air was caused to flow thereto at 100 mL/min, the detector was initialized through heat treatment for 3 minutes.

The sensor temperature was first set to 80° C. While compressed air and 2-ppm NO gas (diluted with nitrogen) were caused to flow thereto at 100 mL/min and 100 mL/min, respectively, a NO gas exposure test was made.

Next, the detector was again initialized through heat treatment at 150° C., and then the sensor temperature was adjusted to 60° C. While compressed air and 2-ppm NO gas (diluted with nitrogen) were caused to flow thereto at 100 mL/min and 100 mL/min, respectively, a NO gas exposure test was made.

Furthermore, the detector was again initialized through heat treatment at 150° C., and then the sensor temperature was adjusted to 40° C. While compressed air and 2-ppm NO gas (diluted with nitrogen) were caused to flow thereto at 100 mL/min and 100 mL/min, respectively, a NO gas exposure test was made.

Additionally, the detector was again initialized through heat treatment at 150° C., and then the sensor temperature was adjusted to 115° C. While compressed air and 2-ppm NO gas (diluted with nitrogen) were caused to flow thereto at 100 mL/min and 100 mL/min, respectively, a NO gas exposure test was made.

Figure 12A:
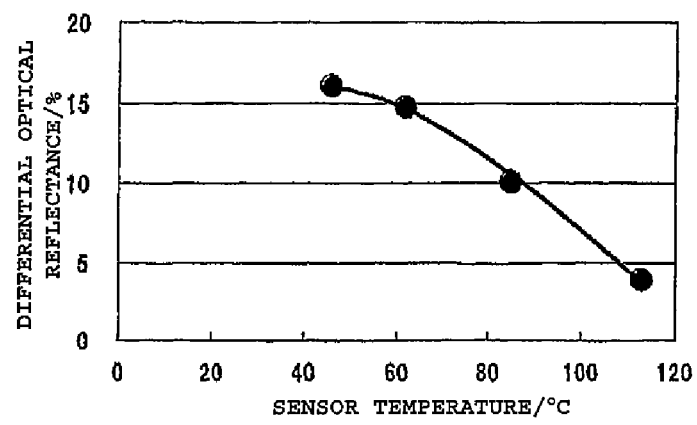
FIG. 12A and FIG. 12B are graphs showing a relationship between the sensor temperature and the NO sensitivity that are obtained from measurement made when a nitric oxide detection element of the present invention is exposed to 1 ppm of NO gas; and a relationship between the sensor temperature and the NO response time obtained therefrom.
Figure 12B:
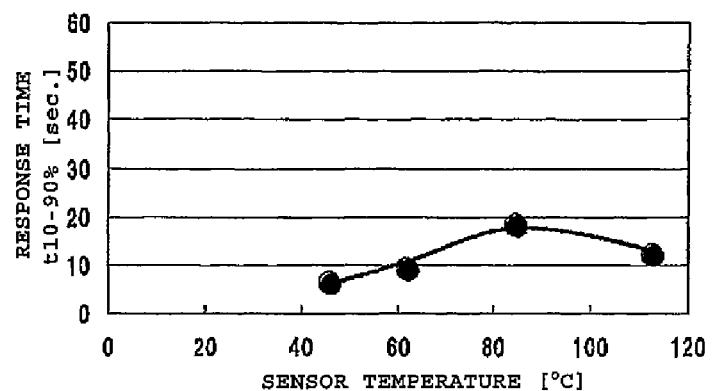

FIG. 12 shows a relationship between the sensor temperature at the time of the NO exposure, and the NO sensitivity; and a relationship between the temperature and the NO response time. From FIG. 12A, it is understood that the NO sensitivity is increased as the sensor temperature is lowered from 115° C. to 40° C. In particular, at a sensor temperature of 40° C., the NO sensitivity is increased by about 1.5 times as compared with that at 80° C., which has been described above. In the meantime, it is understood from FIG. 12B that the NO response time is a maximum value when the sensor temperature is 80° C., and as the temperature is lowered from 80° C. to 40° C., the NO response tends to increase in speed.

INDUSTRIAL APPLICABILITY

The nitric oxide detection element according to the present invention is useful for nitric oxide gas detection in the medical and pharmaceutical fields, drug development, environmental measurement, and chemical safety assessment.

REFERENCE SIGNS LIST

10A Nitric oxide detection element
11 Sensing film
12 Substrate
13 Measurement cell
14 Gas introducing inlet
15 Gas exhaust outlet
16 Light source
17 Photodetector
18 Photo transmitter/photoreceiver
19 Measurement controller
20, 21 Optical fiber
22, 23, 25 Control line
24 Temperature controller
30 Measurement gas
100 Nitric oxide sensing particles
101 Inorganic particles
103 Polymer adhesive
104 Non-ionic surfactant
111 Sensing film portion
112 Peripheral portion

The invention claimed is:
1. A nitric oxide detection element, comprising a substrate, and a sensing film formed on a surface of the substrate,
wherein the sensing film comprises nitric oxide sensing particles, a polymer adhesive and a non-ionic surfactant, and
the nitric oxide sensing particles are formed by adsorbing a dye having a porphyrin skeleton and having as a central metal divalent cobalt onto surfaces of inorganic particles.

2. The nitric oxide detection element according to claim 1, wherein a weight ratio of the polymer adhesive to the inorganic particles is not less than 0.07 g/g and not more than 0.20 g/g.

3. The nitric oxide detection element according to claim 1, wherein a molar-weight ratio of the dye to the inorganic particles is not less than $1.0 \times 10^{-6}$ mol/g and not more than $1.0 \times 10^{-5}$ mol/g.

4. The nitric oxide detection element according to claim 1, wherein a number of cobalt atoms per unit area of the sensing film is not less than $10^{15}$ cm$^{-2}$ and not more than $10^{16}$ cm$^{-2}$.

5. The nitric oxide detection element according to claim 1, wherein a maximum optical absorbance of the nitric oxide detection element is not less than 10% and not more than 30% in an optical wavelength region of 400 nm to 450 nm.

6. The nitric oxide detection element according to claim 1, wherein a molar-weight ratio of the dye to the non-ionic surfactant is not less than $3.0 \times 10^{-6}$ mol/g and not more than $3.0 \times 10^{-4}$ mol/g.

7. The nitric oxide detection element according to claim 1, wherein a weight ratio of the non-ionic surfactant to the inorganic particles is not less than 0.05 g/g and not more than 1 g/g.

8. The nitric oxide detection element according to claim 1, wherein a hydrophilic-lipophilic balance value of the non-ionic surfactant is not less than 13 and not more than 15.

9. The nitric oxide detection element according to claim 1, wherein the inorganic particles are silica or an α-alumina, or a mixture of silica particles and α-alumina particles.

10. The nitric oxide detection element according to claim 1, wherein the inorganic particles are water-repellent treated inorganic particles.

11. The nitric oxide detection element according to claim 1, wherein a particle diameter of the inorganic particles is 6 to 12 μm.

12. The nitric oxide detection element according to claim 1, wherein the dye has trivalent cobalt in addition to the divalent cobalt as the central metal.

13. The nitric oxide detection element according to claim 1, wherein the substrate is a plastic substrate, a ceramic substrate, a metal substrate, paper, a woven fabric or a nonwoven fabric.

14. A nitric oxide detection method, comprising:
a first step of initializing the nitric oxide detection element recited in claim 1 by transforming cobalt contained in the dye into divalent cobalt;
a second step of radiating, after the first step, light to the sensing film of the nitric oxide detection element, and measuring optical absorbance of the sensing film;
a third step of bringing, after the second step, the sensing film into contact with a measurement gas possibly containing nitric oxide;
a fourth step of radiating, after the third step, light to the sensing film and measuring optical absorbance of the sensing film; and
a fifth step of comparing the optical absorbance obtained in the fourth step with the optical absorbance obtained in the second step to determine concentration of nitric oxide contained in the measurement gas.

15. The nitric oxide detection method according to claim 14, wherein the first step of initializing the nitric oxide detection element is performed through a heat treatment, light irradiation or electromagnetic irradiation with microwave.

16. A process for producing a nitric oxide detection element, comprising:
a step of applying, onto a surface of a substrate, a polymer adhesive solution wherein a polymer adhesive is dissolved in a first solvent;
a step of mixing a dye having a porphyrin skeleton and having, as a central metal, divalent cobalt with inorganic particles, a second solvent and non-ionic surfactant to produce a preparation solution containing nitric oxide sensing particles wherein the dye is adsorbed onto surfaces of the inorganic particles, and the second solvent;
a step of adding the preparation solution to the polymer adhesive solution applied onto the surface of the substrate; and
a step of drying the first solvent and the second solvent to form, onto the substrate, a sensing film comprising the nitric oxide sensing particles and the polymer adhesive.

17. The process for producing a nitric oxide detection element according to claim 16, wherein a number of cobalt atoms per unit area of the sensing film is not less than $10^{15}$ cm$^{-2}$ and not more than $10^{16}$ cm$^{-2}$.

18. The process for producing a nitric oxide detection element according to claim 16, wherein the inorganic particles are water-repellent treated inorganic particles.

19. The process for producing a nitric oxide detection element according to claim 16, wherein a particle diameter of the inorganic particles is 6 to 12 μm.

20. The process for producing a nitric oxide detection element according to claim 16, wherein the dye has trivalent cobalt in addition to the divalent cobalt as the central metal.

* * * * *